United States Patent [19]

Tomasch

[11] Patent Number: 5,115,136
[45] Date of Patent: May 19, 1992

[54] ULTRAVIOLET REMOTE VISUAL INSPECTION SYSTEM

[75] Inventor: Michael D. Tomasch, Kew Gardens, N.Y.

[73] Assignee: Olympus Corporation, Lake Success, N.Y.

[21] Appl. No.: 562,741

[22] Filed: Aug. 6, 1990

[51] Int. Cl.$^5$ .............................. G01J 5/04; G01J 5/48
[52] U.S. Cl. .................. 250/461.1; 250/302; 385/117
[58] Field of Search .................. 250/461.1, 302; 350/96.25, 96.26, 96.27, 501; 356/241; 606/7

[56] References Cited

U.S. PATENT DOCUMENTS

| | | | |
|---|---|---|---|
| 3,798,964 | 3/1974 | Misseroni | 73/117.2 |
| 3,852,526 | 12/1974 | McCullough et al. | 358/100 |
| 3,978,720 | 9/1976 | Ford | 73/116 |
| 3,995,157 | 11/1976 | Holub et al. | 250/302 |
| 4,065,059 | 12/1977 | Jablin | 239/750 |
| 4,175,545 | 11/1979 | Termanini | 128/666 |
| 4,207,874 | 6/1980 | Choy | 128/6 |
| 4,412,177 | 10/1983 | Petrini et al. | 324/226 |
| 4,508,369 | 4/1985 | Mode | 285/39 |
| 4,562,838 | 1/1986 | Walker | 606/42 |
| 4,621,193 | 11/1986 | Van Hoye | 250/302 |
| 4,628,207 | 12/1986 | Elfert et al. | 250/461.1 |
| 4,640,124 | 2/1987 | Diener et al. | 73/116 |
| 4,643,022 | 2/1987 | Werlberger et al. | 73/117.3 |
| 4,669,465 | 6/1987 | Moore et al. | 606/7 |
| 4,696,544 | 9/1987 | Costella | 350/96.26 |
| 4,791,293 | 12/1988 | Barriere | 250/302 |
| 4,846,171 | 7/1989 | Kauphusman et al. | 606/15 |
| 4,918,982 | 3/1990 | Pischinger et al. | 73/116 |

FOREIGN PATENT DOCUMENTS

| | | | |
|---|---|---|---|
| 59-172621 | 9/1984 | Japan | 350/96.26 |
| 60-15618 | 1/1985 | Japan | 350/96.26 |
| 61-80218 | 4/1986 | Japan | 350/96.26 |

OTHER PUBLICATIONS

Briggs, W. D., "Flaw Location with Turco Dy z-chek", Turco Products, Inc. of Wilmington, Calif., Jul. 1959.

*Primary Examiner*—Constantine Hannaher
*Assistant Examiner*—Jacob M. Eisenberg
*Attorney, Agent, or Firm*—Kenyon & Kenyon

[57] ABSTRACT

The invention provides an ultraviolet remote visual inspection system which enables the operator to detect minute cracks and hairline flaws in normally inaccessible places of manufactured parts. The system includes a fiberscope in combination with a source of white light and ultraviolet light and a plurality of cannisters for holding dye penetrant and other materials which can be used to facilitate the inspection. The fiberscope includes an articulated probe having a working channel, an ultraviolet light guide and an objective lens. The plurality of cannisters are connected to the working channel through a manifold. Dye penetrant, cleaning solution, drying air and developer can be individually delivered to the remote surface to be tested through the working channel from the cannisters. The fiberscope is provided with an adjuster for bending the articulated probe in different directions to facilitate application of the aforesaid materials and the subsequent visual inspection. Dye penetrant which is entrapped in cracks fluoresces brightly when illuminated by the ultraviolet light so that the cracks are easily identified.

11 Claims, 2 Drawing Sheets

ULTRAVIOLET REMOTE VISUAL INSPECTION SYSTEM

BACKGROUND OF THE INVENTION

1. Field of the Invention

The invention relates to a system for use in detecting surface defects in manufactured parts and the like. More particularly, the invention relates to a system which enables an inspector to detect hairline cracks and flaws in otherwise inaccessible and remote locations through the use of ultraviolet light and fluorescent dye penetrant.

2. Description of Background Art

The use of dye penetrants to detect small flaws in critical manufactured components such as jet engine turbine blades is well known. Typically, flaw detection by the dye penetrant method requires the following sequence of steps.

First, the object to be tested is cleaned thoroughly, using a vapor degreaser, for example. Next the object is immersed in a dye penetrant solution which contains a solvent and a dye, typically one which fluoresces brightly when irradiated by long-wave ultraviolet radiation, in the approximate range of 300 nm to 400 nm. Alternatively, dye penetrant may be sprayed upon the surface of the object to be tested. Third, excess dye penetrant solution is removed from the surface of the part with the aid of another solution, and emulsifier. The part is then washed and dried. Finally, the part under test is illuminated with a source of ultraviolet radiation. Dye penetrant which has been entrapped in small voids such as cracks, seams or porous areas fluoresces brightly when illuminated by the ultraviolet radiation source, providing a visual indication of small defects which would otherwise escape visual detection. Sometimes a developer solution is applied to the surface of the part after that surface has been cleansed of excess dye penetrant solution. The function of the developer solution is to draw up to the surface of the part, by capillary action, dye which has been entrapped in voids some distance below the surface. This makes the dye and therefore the void more readily visible.

The dye penetrant inspection processes just described are generally effective for detecting small surface flaws in manufactured parts. However, minute cracks and flaws can exist in places which are inaccessible to conventional probes. Thus, the spray method of applying dye penetrant can miss remote hard-to-reach locations where cracks and flaws may exist. Although the immersion method of applying penetrant is more pervasive it has the drawback that the part to be tested must be preheated and remain immersed in the dye for a substantial period. A further drawback is that large and cumbersome parts require large immersion tanks and large volumes of dye penetrant solution.

Another disadvantage of fluorescent penetrant crack detection is several different instruments are required to accomplish each of the forementioned steps. After the dye penetrant is applied separate instruments are required to remove excess penetrant, to dry the surface to be examined, to apply the developer and to illuminate the surface to be examined with ultraviolet light for inspection. The manipulation and handling of these different instruments can be cumbersome and time consuming for a single operator.

Accordingly, it is an object of the invention to provide an interactive and reactive ultraviolet remote visual inspection system which allows for the detection of cracks in places not normally accessible to the eye.

It is a further object of the invention to provide a system of the type described in the previous paragraph wherein a single apparatus can be used for several different functions including illumination of the surface to be examined with white light, injection of dye penetrant, washing away of excess penetrant, drying the surface, injection of developer, illumination with ultraviolet light and visual inspection.

It is yet a further object of the invention to provide an apparatus of the type described in the previous paragraph which includes an articulated probe to facilitate visual inspection of remote internal areas such as passages in castings.

Additional objects and advantages of the present invention will be apparent to those skilled in the art by reading the accompanying specification and claims in view of the drawings.

SUMMARY OF THE INVENTION

The invention provides an ultraviolet remote visual inspection system which enables the operator to detect minute cracks and hairline flaws in normally inaccessible and/or internal places of manufactured parts. The system includes a fiberscope in combination with a source of white light and ultraviolet light and a plurality of cannisters for holding dye penetrant and other materials which can be used to facilitate the inspection. The fiberscope includes an articulated probe having a working channel, an ultraviolet light guide and an objective lens. The plurality of cannisters are connected to the working channel through a manifold. Dye penetrant, cleaning solution, drying air and developer can be individually delivered to the surface to be tested through the working channel from the cannisters. The fiberscope is provided with an adjuster for bending the articulated probe in different directions to facilitate application of the aforesaid materials and the subsequent visual inspection. Dye penetrant which is entrapped in cracks fluoresces brightly when illuminated by the ultraviolet light so that the cracks are easily identified.

DETAILED DESCRIPTION

Figure 1:
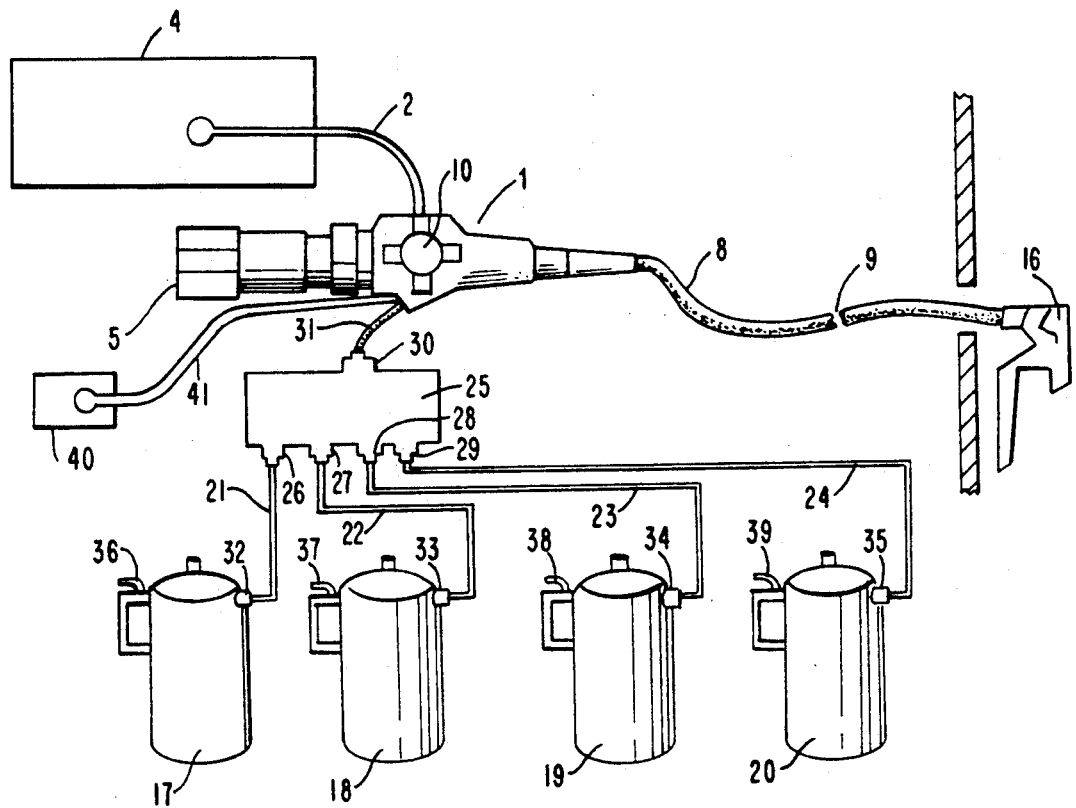
FIG. 1 is a perspective view of the ultraviolet remote visual inspection system in accordance with the invention.

Referring to FIG. 1 an ultraviolet remote visual inspection system of the invention is depicted. The system includes a light guide or fiberscope generally depicted at 1. The light guide must be capable of carrying ultraviolet (UV) light efficiently and preferably white light as well. Standard glass fibers used in conventional fiberscopes and borescopes do not carry UV light effectively; there is too much loss of illumination. Liquid light guides have been found to transmit UV light very efficiently. Quartz fibers are also very effective, but they tend to be fragile.

Figure 2:
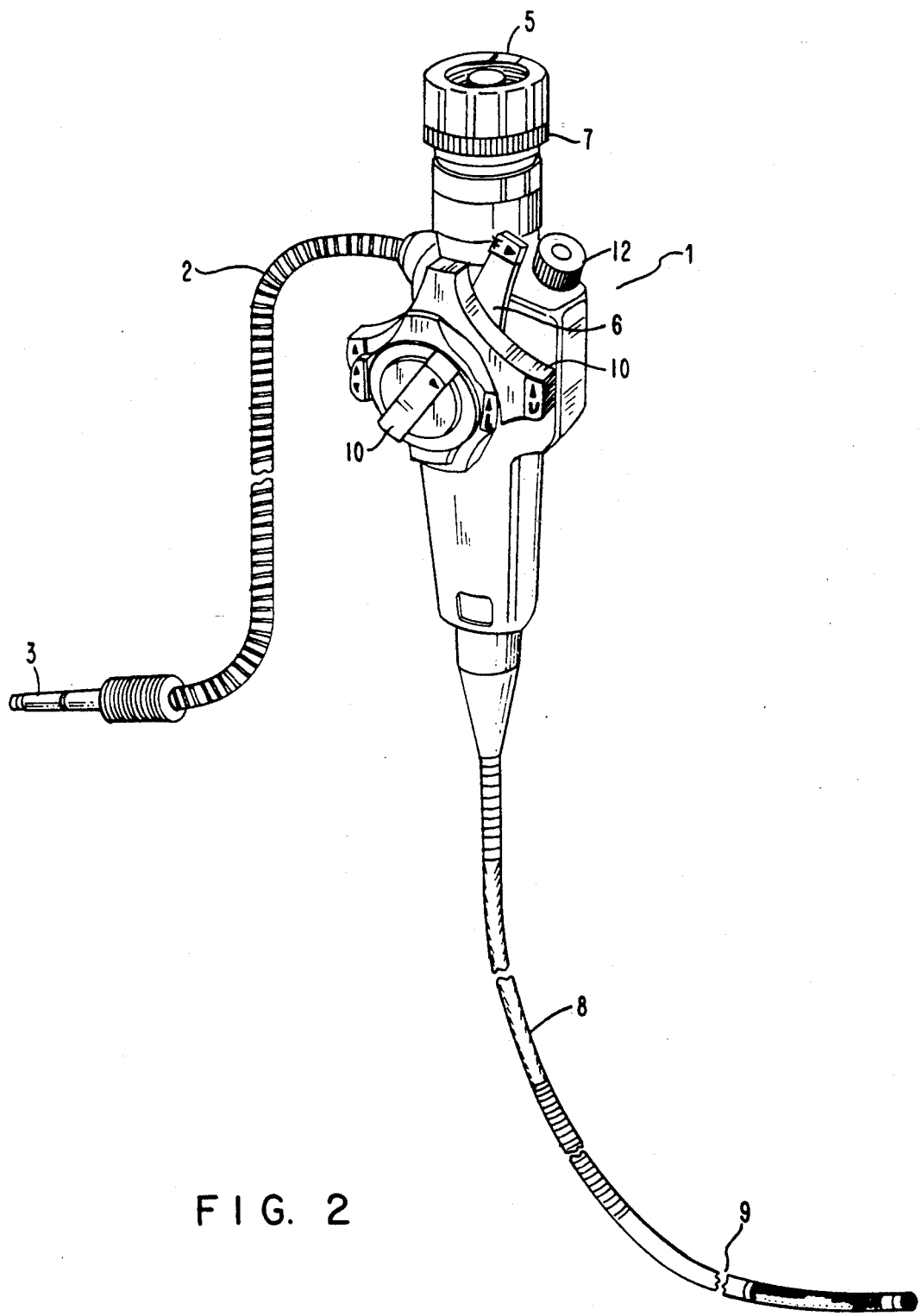
FIG. 2 is a perspective view of a fiberscope which can be used in the ultraviolet remote visual inspection system of the invention.

A preferred fiberscope for use with the invention is the new modified model IF7D3X3-26 (UV) fiberscope available from Olympus Corporation. This light guide employs a silica glass fiber and special lenses which carry both UV and white light very efficiently. A detailed view of such a fiberscope is illustrated in FIG. 2. The fiberscope includes a light guide cable 2 having a connector 3 for connection to a source of UV light 4 (see FIG. 1). The fiberscope includes an ocular or eyepiece 5 through which a visual inspection can be made. The eyepiece 5 has a yellow filter (not illustrated) for protection. A diopter adjustment ring 7 is provided for controlling focus of the fiberscope to the eye.

The fiberscope 1 includes a probe section or insertion tube 8. The insertion tube 8 is preferably articulated so that it is provided with one or more joints 9 at which bending can occur. Bending of the insertion tube in various directions is controlled by one or more adjustment dials 6, 10 which may be provided with locking means for locking the probe in a certain position.

Figure 3:
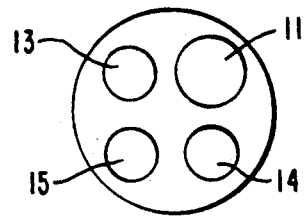
FIG. 3 is a cross-sectional view of the probe of the fiberscope used in the system of the invention.

The fiberscope 1 is provided with an internal fluid proof working channel 11 (see FIG. 3, a cross-sectional view of the insertion tube 8). The working channel 11 is a conduit for the materials used in the inspection including the dye penetrant, cleaning solution, developer and drying gas. The working channel 11 extends from a receiving connection 12 of the fiberscope to the end tip of the insertion tube 8. The working channel is preferably 1 to 3 mm in diameter.

Referring to FIG. 3, a cross-sectional view of the insertion tube 8 illustrates light guides 13, 14 which emanate from the light guide cable and continue through the insertion tube to its tip and which can include a special lens to maximize UV output. Insertion tube 8 also includes an objective lens 15 for focusing an image of the surface 16 (see FIG. 1) to be examined.

The UV remote visual inspection system of the invention includes a source of UV light and preferably a source of white light. The white light is used to illuminate the area during the preparatory steps of applying the dye penetrant and the developer.

A preferred source of both UV light and white light for use in the invention is the UV-6250 light source available from Olympus Corporation. The UV-6250 light source produces both ultraviolet illumination and white light. When used with the new modified Olympus 7 mm IF7D3X3-26 (UV) fiberscope described above, the UV output of the combination is approximately 2,000 microwatts per square centimeter at a distance of one inch from the tip of the scope. This is more than five times the output of other conventional UV light sources and provides sufficient UV light for the system of the invention. The UV-6250 has a halide discharge lamp which produces white light with a high concentration of energy in the 350 to 380 nm spectrum. The UV-6250 includes a connector plug which is adapted to be connected to the light guide cable 2 of the fiberscope. A filter is interposed between the lamp and the light guide connector plug, which eliminates virtually all of the spectrum above 380 nm.

The inspector can switch between white light and UV light at will, using white light for insertion of the fiberscope probe and for general orientation of the tip in the worksite. The inspector also has a choice of several filters, which are mounted either individually or which are selectable via a rotating turret, for UV spectra consistent with the fluorescence of different developers as known to those skilled in the art.

The UV remote visual inspection system of the invention includes a special delivery system for the materials used in the inspection which allows the inspector to perform some or all of the preparation steps with the fiberscope. The delivery system includes a number of cannisters 17, 18, 19, 20 for holding the materials used. The materials are stored under pressure and can be discharged through a sealable orifice 32, 33, 34 and 35 by activating a release button 36, 37, 38 and 39. Preferably the cannisters are rechargeable. One preferred cannister which can be adapted for use in the invention is the Model A "Sure Shot Sprayer" which is commercially available from the Milwaukee Sprayer Mfg. Co.

The cannisters 17, 18, 19 and 20 can include, for example, dye penetrant, compressed air, cleaning solution (e.g., water) and developer. It should be appreciated that fewer or more cannisters may be used depending upon the number of steps to be performed using the fiberscope. For example, depending upon the condition of the surface to be examined it may be desirable to clean off the surface with a strong cleaner such as methylethyl ketone prior to injection of the dye. This cleaning step may be conducted with the fiberscope by including an additional cannister of cleaner.

Each of the orifices of the cannisters 17, 18, 19 and 20 is connected via a line 21, 22, 23 and 24 to a manifold 25. Lines 21, 22, 23 and 24 may be plastic tubing. For connection to the lines, manifold 25 is provided with a corresponding number of input fittings 26, 27, 28, 29. The input fittings should be such that they lock the tubing and seal it up to the working pressure in the cannisters. Preferred fittings for this purpose are Polymatic ® fittings which are described in detail in U.S. Pat. No. 4,508,369.

Manifold 25 is also provided with an output fitting 30 which is connected with the receiving connection 12 of the fiberscope through line 31. To discharge material from a particular cannister, the operator merely presses the release button 36, 37, 38 and 39 of that cannister. Material from a cannister is delivered to the working channel 11 of the fiberscope from output fitting 30 through line 31.

In operation, the ultraviolet remote visual inspection system of the invention is used to detect the presence of small cracks and flaws on the surface of metallic parts, such as for example, gas turbines, internal combustion engines, pipelines, process tubing, pressure vessels, remote welds, etc . . . The probe 8 of the fiberscope is inserted into the worksite. The surface to be examined is first cleaned. Through the eyepiece and with aid of white light the operator would target the area to be cleaned and discharge water from one of the cannisters to that area. If desired, the invention can also be provided with a cannister of a stronger cleaner such as methylethyl ketone. The next step is to dry the surface to be inspected with a drying gas such as compressed air which is discharged from the cannister holding the same.

After drying, the dye penetrant is discharged from its cannister and injected into the worksite. The dye penetrant must be one which fluoresces upon exposure to UV light. A water soluble dye is preferred because excess dye can then be rinsed away with water. Such dyes are known to those skilled in the art. MIL SPEC F-134D powder is a preferred commercially available dye.

After injection of the dye the operator should wait 10-15 minutes for the dye to penetrate any flaws or cracks. Excess penetrant is then washed away by using the fiberscope to inject water or other cleanser into the worksite. Water is delivered from the water cannister via the working channel.

A developer is optionally applied to the surface to promote the drawing of the penetrant to any hairline cracks. The developer can be applied through the working channel of the fiberscope from a cannister holding the developer. Talc powder is a suitable developer. The developer should be allowed to set for 5 to 10 minutes before an inspection is made. Excess developer can be washed off with water injected by the fiberscope or through the use of an accessory pump.

To check for flaws and cracks the UV light source is activated and a visual inspection is made through the eyepiece of the fiberscope. The probe can be manipulated and bent at its joints to inspect remote locations using the adjuster controls on the fiberscope. Since the dye penetrant fluoresces or produces visible light when illuminated by the UV light, hairline cracks which are difficult to see under normal conditions are readily seen.

The luminescent effect which results upon exposure to UV light can be enhanced by simultaneously illuminating the area to be inspected with both UV light and white light. It has been stated above that UV light source 4 can also be a source of white light. However, conventional sources of both UV light and white light cannot effectively provide simultaneous illumination and transmission of both types of light. Simultaneous exposure to both UV light and white light can be achieved by providing the system of the invention with an additional source of white light 40 (see FIG. 1) which must be separate from the source of UV light 4. The separate source of white light 40 may be connected to fiberscope 1 by directly running a light guide cable 41 from the light source into receiving connection 12, through working channel 11 to the tip of probe section 8. Alternatively, the separate source of white light can be connected through an input of manifold 25 via a liquid light guide tube which can feed and continue through the working channel of the fiberscope.

One or more working tools may be used to assist in the inspection. For example, power brushes, cutting tools and grinding tools may be used to facilitate cleaning and preparation of the surface to be inspected. In accordance with the invention, cables used to connect these tools to a motor may be run through the working channel of the fiberscope.

In the foregoing specification, the invention has been described with reference to specific exemplary embodiments thereof. It will, however, be evident that various modifications and changes may be made thereunto without departing from the broader spirit and scope of the invention as set forth in the appended claims. The specification is accordingly to be regarded in an illustrative rather than a restrictive sense.

What is claimed is:

1. An apparatus for detecting cracks in a remote surface through the use of a dye penetrant which fluoresces upon illumination with ultraviolet light comprising:

a fiberscope including a probe for receiving an image of a surface, a lens for focusing an image received by the probe, an eyepiece for viewing an image, a means for guiding ultraviolet light through the probe to a surface, and a channel means for allowing for the transportation of material through said probe to a surface;

a source of ultraviolet light communicating with the means for guiding ultraviolet light of the fiberscope;

a first cannister having a sealable orifice capable of holding a dye penetrant under pressure, said first cannister including a means for releasing dye penetrant under pressure through said orifice;

a second cannister having a sealable orifice capable of holding a liquid, solid or gaseous material under pressure, said second cannister including a means for releasing the material under pressure through said orifice;

a manifold having at least two input fittings and an output fitting;

tubing means joining the orifice of the first cannister to an input fitting of the manifold;

tubing means joining the orifice of the second cannister to an input fitting of the manifold; and tubing means joining the output fitting of the manifold to the channel means of said fiberscope.

2. An apparatus according to claim 1 further comprising a source of white light wherein the fiberscope includes a means for guiding white light through the probe to a surface, said source of white light communicating with said means for guiding white light.

3. An apparatus according to claim 2 wherein said first cannister holds dye penetrant and said second cannister holds a developer.

4. An apparatus according to claim 3 wherein the manifold has at least four input fittings, the apparatus further comprising a third cannister and a fourth cannister, each having a sealable orifice and capable of holding a liquid, powder or gaseous material under pressure, and tubing means connecting the orifice of each of the third cannister and the fourth cannister with an input fitting of the manifold.

5. An apparatus according to claim 4 wherein the third cannister holds compressed air and the fourth cannister holds water.

6. An apparatus according to claim 1 wherein the probe of the fiberscope is articulated.

7. An apparatus according to claim 6 wherein the fiberscope includes means for bending and adjusting the probe at points of articulation.

8. An apparatus according to claim 1 wherein the means for guiding ultraviolet light can also guide white light and wherein the source of ultraviolet light also includes a source of white light.

9. An apparatus according to claim 1 further comprising a source of white light which is separate from the source of ultraviolet light, a white light guide joining the source of white light to the channel means of the fiberscope, said white light guide extending through the channel means.

10. An apparatus according to claim 9 wherein the white light guide is a liquid light guide.

11. An apparatus according to claim 9 wherein the manifold has at least three input fittings and wherein the white light guide is connected to an input fitting, extends through the manifold, through the output fitting of the manifold and to the channel means.

* * * * *